(12) United States Patent
Drevik

(10) Patent No.: US 6,398,770 B1
(45) Date of Patent: Jun. 4, 2002

(54) ABSORBENT ARTICLE SUCH AS A SANITARY TOWEL, AN INCONTINENCE PROTECTOR, A PANTYLINER OR THE LIKE

(75) Inventor: Solgun Drevik, Mölnlycke (SE)

(73) Assignee: SCA Hygiene Products AB, Gothenburg (SE)

( * ) Notice: Subject to any disclaimer, the term of this patent is extended or adjusted under 35 U.S.C. 154(b) by 0 days.

(21) Appl. No.: 09/554,183

(22) PCT Filed: Nov. 17, 1998

(86) PCT No.: PCT/SE98/02066

§ 371 (c)(1),
(2), (4) Date: May 11, 2000

(87) PCT Pub. No.: WO99/25282

PCT Pub. Date: May 27, 1999

(30) Foreign Application Priority Data

Nov. 19, 1997 (SE) ................................................ 9704231

(51) Int. Cl.[7] .............................................. A61F 13/15
(52) U.S. Cl. ............................. 604/385.01; 604/385.24; 604/385.27; 604/385.17; D24/124
(58) Field of Search ........................ 604/385.01, 385.24, 604/385.27, 385.17; D24/124

(56) References Cited

FOREIGN PATENT DOCUMENTS

| EP | 0 155 515 | 9/1985 |
|----|-----------|--------|
| EP | 0 162 451 | 11/1985 |
| EP | 0 302 523 | 2/1989 |
| EP | 0 335 253 | 10/1989 |
| WO | WO 96/20679 | 7/1996 |
| WO | WO 97/07764 | 3/1997 |

*Primary Examiner*—John J. Calvert
*Assistant Examiner*—Angela J. Grayson
(74) *Attorney, Agent, or Firm*—Young & Thompson

(57) ABSTRACT

Absorbent article, such as a sanitary towel, an incontinence protector or a pantyliner, which article has essentially an elongate shape, with a longitudinal direction (34) and a transverse direction (35), and has two end portions (10, 11) and a central portion (12) situated between the end portions (10, 11), and on which article there is arranged elastic (18) which gives the article a cup-shaped part (14) at the one end portion (10) and a ridge-like elevation (15) at the other end portion (11).

11 Claims, 8 Drawing Sheets

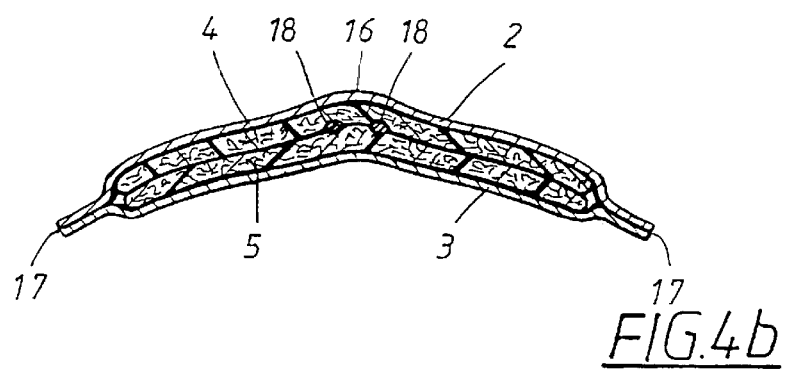
FIG. 4a
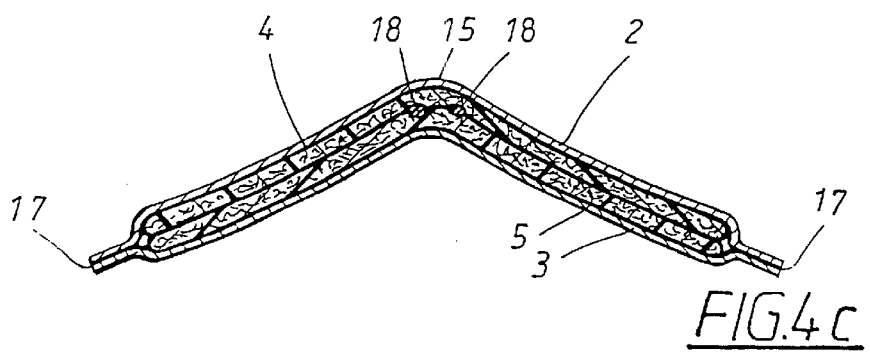
FIG. 4b
FIG. 4c
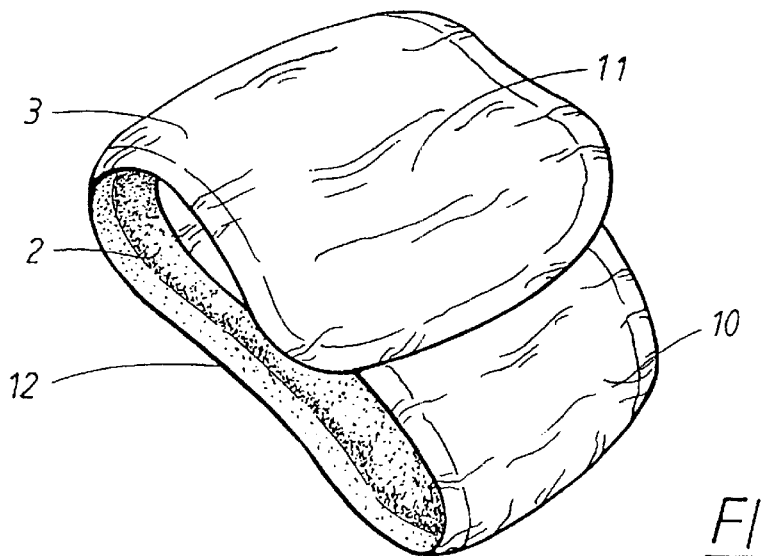
FIG. 5

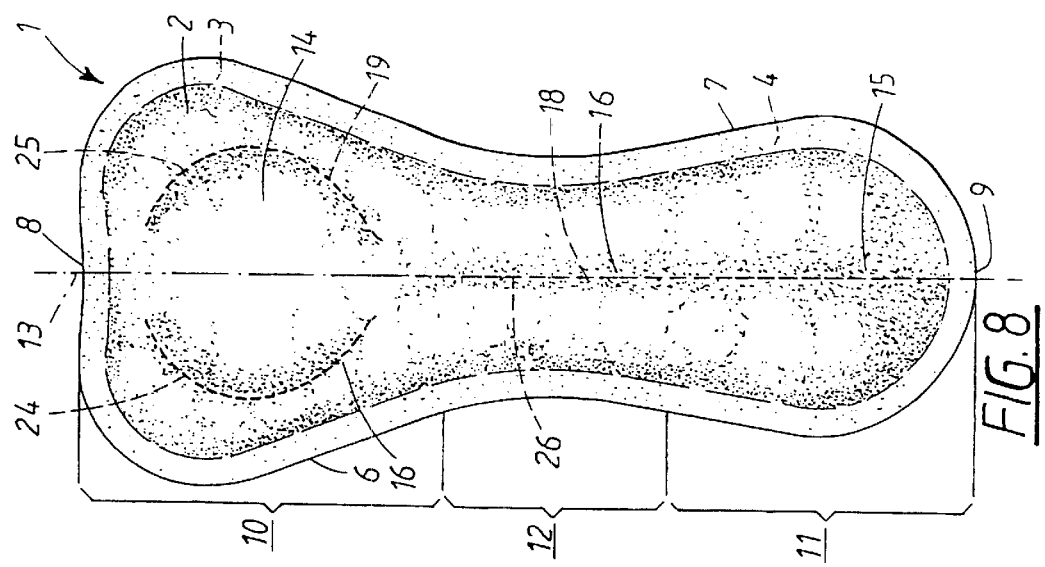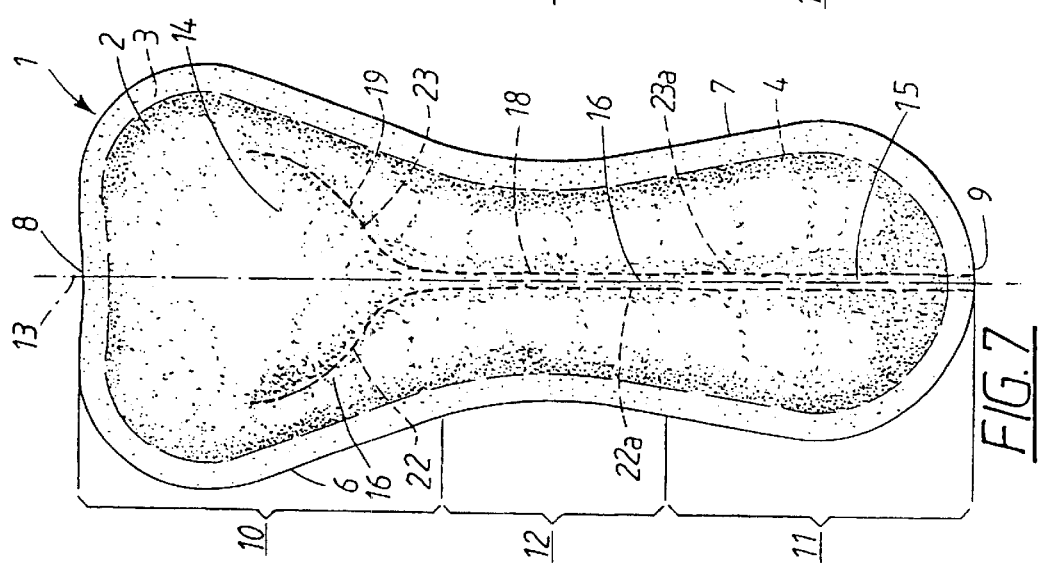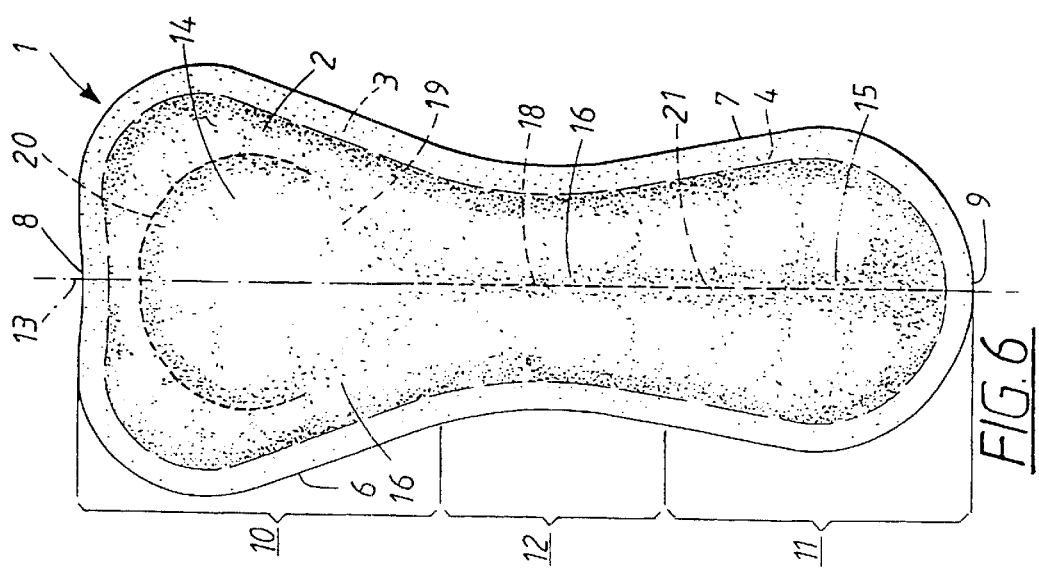

ABSORBENT ARTICLE SUCH AS A SANITARY TOWEL, AN INCONTINENCE PROTECTOR, A PANTYLINER OR THE LIKE

TECHNICAL FIELD

An absorbent article such as a sanitary towel, an incontinence protector or a pantyliner, which article has essentially an elongate shape, with a longitudinal direction and a transverse direction, and has two end portions and a central portion situated between the end portions.

BACKGROUND

Conventional absorbent articles of the type mentioned above usually have a flat shape. Since the female pubic region does not have a corresponding flat appearance, problems can occur when applying and wearing such articles. The contact of the article against the body is not optimum, and when a gap develops there is a great risk of leakage. In order to solve this problem, it has been proposed to make the absorbent articles cup-shaped rather than flat. By and large, this shape provides a better fit to the contours of the body. The cup shape is produced, for example, by arranging elastic in the longitudinal edges of the article, or the article is moulded in a cup shape. EP 155,515 describes how an absorbent article is given a cup-shaped appearance by arranging elastic in the longitudinal side edges of the article. WO 96/20679 describes an absorbent article which comprises a resilient component and tensioning member for giving the article a cup-shaped appearance.

A problem with articles of the abovementioned type is that they do not adapt to the anatomy of the user particularly well, but simply have a general cup-shaped appearance. An article shaped in this way does not provide a good fit against the body. In addition, a gap can easily occur between the user's body and the user's briefs since most women, during menstruation, wear briefs which are of poor quality from the outset or are of poor quality because they are old ones. Unless either the absorbent article or the briefs are able to maintain a good contact with the user's body, there is a great risk of menstruation fluid leaking past both the absorbent article and the briefs.

WO 97/07764 discloses an incontinence product having longitudinally extending elastication means providing a longitudinal ridge in the central portion of the product. The product has a generally curved shape in the longitudinal direction and is stated to provide improved body contact in the central area of the product.

EP 0 335 253 discloses an absorbent article which is provided with a deformation element which causes the article to assume a predetermined shape in response to laterally acting forces.

EP 302,523 describes an absorbent article which has a three-dimensional, anatomically designed shape. The article has an end portion of flat or concave shape and an end portion which is provided with an elevation. The flat or concave end portion is intended to be placed outside the user's mons pubis, and the end portion comprising the elevation is intended to fit the user's buttocks. The three-dimensional configuration of the article is obtained by folding a fairly stiff absorption body. To make the elevation permanent, the reverse side of the article is provided with an adhesive surface at the end portion which is to present the elevation. When the elevation has been formed, it is maintained with the aid of the adhesive.

A problem with a construction of this type is that the three-dimensional shape can be hard and uncomfortable for the user. Moreover, it is difficult to package and transport a stiff three-dimensional product. It takes up a lot of space during transport and when on sale, and it can be inconvenient for the user to carry around a sanitary towel or an incontinence protector which cannot be folded and which therefore cannot be concealed in the hand or, at worst, cannot even be fitted in a handbag.

OBJECT OF THE INVENTION

The object of the invention is to remedy the abovementioned problems and to make available an absorbent article which provides a good fit against the user's body, and which article is comfortable to use and easy to transport.

BRIEF DESCRIPTION OF THE INVENTION

According to the invention, an article of the type discussed in the introduction, and in which the problems associated with previously known articles of this kind have been eliminated, is distinguished by the fact that elastic is arranged on the article and gives the article a cup-shaped part at one end portion and a ridge-like elevation at the other end portion.

According to one embodiment of the invention, the elastic is arranged in a loop in the end portion which has a cup-shaped part. Arranging the elastic in a loop contributes to giving the end portion its cup shape.

According to another embodiment of the invention, the elastic is arranged as a continuous thread or band running through the entire article.

In order to further improve the anatomical fit against the user's body for an article with a ridge-like elevation which extends across both the central portion of the article and across one end portion thereof, according to one embodiment of the invention the ridge-like elevation in the end portion has a steeper inclination towards the centre line of the article than does the ridge-like elevation in ad the central portion, as seen from a long side of the article.

According to one embodiment of the invention, the elastic in the central portion is arranged in an essentially straight line along the centre line of the article.

According to a further embodiment of the invention, the elastic is arranged as a continuous thread or band running in a loop through the entire article. In this case, the elastic has two halves which in the longitudinal direction are arranged symmetrically around the centre line of the article. The continuous band or thread can be laid overlapping, i.e. with the halves crossing each other, at the transition between the end portion which has the cup-shaped part and the central portion, an at the transition between the central portion and the end portion which has the ridge-like elevation.

According to yet another embodiment of the invention, the article can have at least one fold line. Such a fold line can be arranged on the underside of the article below the ridge-like elevation in the end portion, in order to facilitate the shaping of the ridge-like elevation.

DETAILED DESCRIPTION OF THE INVENTION

The abovementioned problems are solved by means of the present invention. This is achieved by the fact that elastic is arranged on the article and gives the article a cup shape at one end portion and a ridge-like elevation at the other end portion. When an article according to the invention is placed on the user with the cup-shaped end portion towards the front, that is to say over the mons pubis, and with the ridge-like end portion towards the back, that is to say towards the user's bottom, the article will fit naturally to the user's anatomy and will therefore by itself also come to lie fully against the user's body. The cup shape of the front end portion will surround the mons pubis during use, and the ridge-like elevation of the rear end portion will fit in the cleft between the user's buttocks. In this way, sealing is obtained at the front, which is required in particular when the user leans forwards or is lying on her stomach, and also sealing at the rear, in particular when the user leans backwards or is lying on her back. Thus, this design affords considerably better protection against leakage than does a generally cup-shaped appearance of an absorbent article which is not fully adapted to the user's genitals.

An absorbent article according to the invention has a top side and an underside, the top side being liquid-permeable and the underside being liquid-impermeable. The liquid permeability and liquid impermeability, respectively, are usually obtained by the respective side being provided with a layer which is liquid-permeable or liquid-impermeable. The liquid-permeable top side of the article is intended during use to be directed towards the user, and the liquid-impermeable underside is intended during use to be directed away from the user. It is the top side of the article which will have a cup-shaped part at one end portion, a ridge-like elevation at the other end portion, and, if appropriate, a ridge-like elevation in the central portion.

The central portion also preferably has a ridge-like elevation. Because the anatomical shapes are different at the different areas of the user's body against which the rear end portion and central portion are to fit, the ridge-like elevation of the end portion has a steeper inclination in relation to the centre line of the sanitary towel than does the ridge-like elevation of the central portion. The centre line of the sanitary towel signifies an imaginary line which is placed in the longitudinal direction of the sanitary towel, at an equal distance from both long sides of the sanitary towel. While the elevation of the central portion can be flat or incline very slightly in relation to the centre line, it is important that the elevation of the end portion slopes more steeply in relation to the centre line to ensure that the sanitary towel will fit the cleft between the user's buttocks.

Since the user's vestibule will be the part of the body which bears against the centre portion, the central portion of the article should have a cross-section with an elevation at the centre. An elevation in the central portion can be extremely important for preventing leakage, since the sanitary towel can take up the menstruation fluid even as it leaves the body. Since the space which is to be filled by the elevation on the central portion has the approximate shape and size of half a walnut, then, according to the invention, more absorption material can also be placed in the area around the elastic in the central portion. It is also possible to place a further separate absorption body on top of the surface of the sanitary towel at its central portion. A further alternative is to let the two elastic threads run slightly away from each other across the central portion. In this way a wider elevation is obtained which is better adapted to the user's vestibule.

The fact of an elevation being flat means that it essentially follows a centre line through the article when the latter is considered from one long side. That is to say that the centre line and elevation are parallel as seen from one long side of the article. The fact of an elevation sloping in relation to the centre line when the article is considered from a long side means that the centre line and the elevation form an angle between each other. The greater the angle, up to 90°, the greater is the inclination of the elevation. If the angle of the elevation of the end portion in relation to the centre line is 45°, for example, and the angle of the elevation of the central portion is 20°, then the elevation of the end portion slopes more than that of the central portion. The ridge-like elevations of the central portion and of the end portion advantageously consist of a single continuous elevation of varying inclination. However, for reasons of comfort, some users may object to having an elevation in the central portion, and for this reason it may sometimes be appropriate to omit such an elevation.

As has been described above, the three-dimensional anatomical configuration of the article according to the present invention is obtained by means of the article being provided with elastic. By elastic we mean material which exhibits such elasticity that it can be stretched to an elongation of at least 100% of its unstretched, relaxed length, that is to say to a length which is at least twice its unstretched length, and can return, after the stretching force is released, to at most a 10% elongation of its original unstretched length. The elastic material can consist of natural rubber, synthetic rubber or a mixture thereof, styrene block polymers, polyurethane rubber, elastic polyesters or elastic polyolefins.

The elastic can advantageously be arranged between the surface layer of the article and the layer lying nearest the surface layer, that is to say the intake layer or absorption layer. It is also possible, however, to arrange the elastic between other material layers, for example between the intake layer of the article and its absorption layer. The elastic can also be arranged with different tensioning in different parts in order to obtain different inclinations of the elevations in the central and end portions.

The elastic thread or band can also be laid in different ways in order to obtain different effects. The elastic is advantageously arranged along a longitudinal centre line on the end portion which has the ridge-like elevation. As has already been mentioned, the central portion too can have a ridge-like elevation. The elastic in the central portion is expediently arranged in an essentially straight line along the centre line of the article. The embodiments with elastic along the centre line can advantageously be combined with the different variants of elastication in the cup-shaped end portion.

According to one embodiment of the invention, the elastic is arranged in a U-shape in the end portion which has a cup-shaped appearance. That is to say the elastic broadly speaking follows the outer contour of the end portion, and the opening of the U-shape faces the central portion of the article. According to yet another embodiment of the invention, the elastic is arranged in two mirror-image loops which each follow the outer contour of the long sides of the end portion which has the cup-shaped part.

The elastic in the end portions and in the centre portion can consist of a single continuous loop, with the outer ends in the end portion which has the ridge-like elevation. Alternatively, the elastic can consist of two elastic threads which run in mirror image in the longitudinal direction of the article. In this case, the elastic in the end portion having the cup shape can be arranged in an essentially complete circle. Alternatively, the elastic in the end portion having the cup shape can have the shape of a semi-circle, where that part of the end portion nearest the short side of the article does not have any elastic. As with the above-described circle shape, the semi-circle is not complete either, as it consists of the two elastic loops.

In the case where the elastic consists of a continuous loop, then, in the central portion of the article and in the end portion having the ridge-like elevation, it can run in two parallel thread parts. Alternatively, the loop of elastic can be laid overlapping at one or more points. For example, the loop can be laid overlapping at the transition between the central portion and the end portion which has the cup-shaped part. The loop of elastic can also be laid overlapping a second time at the transition between the central portion and the end portion which has the ridge-like elevation. By crossing the loop of elastic, an even better adaptation to the different parts of the user's anatomy can be obtained.

To ensure that the elastic will be able to shape the article, the components included in the article should be relatively soft and pliable. A three-dimensional article which is produced by shaping a stiff material may be felt by the user to be hard and uncomfortable. An advantage of obtaining the three-dimensional nature with the aid of elastic instead of by shaping a stiff material is that a softer and more pliable, anatomically shaped article is obtained. In addition, a still further improved adaptation to the body can be achieved by using the elastic together with soft materials. Such an article is resilient and is more pliable and can therefore adapt in cases where the original shape of the article does not have a completely perfect anatomical configuration. Such fine adjustment is not possible with a stiff article. An elastic three-dimensional article also follows the user's movements more readily than does a stiff article. Moreover, it is difficult to package and transport a stiff three-dimensional article. An article according to the invention provided with elastic is advantageously folded in three parts at the time of packaging and therefore takes up a small amount of space during transport and at the point of sale. It is also an advantage when the user wishes to carry the article around, since it is easy to conceal in the hand, in a pocket or a handbag. The article can of course be folded in another way, for example it can be folded in two or four parts. Rather than creating problems, as in the case of stiff articles, it is an advantage to fold an article which comprises elastic. The folding relieves the elastic during storage, which means that the useful life of the elastic increases considerably.

The absorbent article according to the invention advantageously has a surface layer intended to be directed towards the body, a reverse layer, and an absorption layer situated between the surface layer and the reverse layer. The article can also have an intake layer in order to increase the rate of intake, which layer is arranged between the surface layer and the absorption layer. It may be useful to provide the article with so-called fold lines. These fold lines have two purposes. On the one hand, they can stiffen a soft material so that, for example, the cup shape in the one end portion is maintained, or so that the central portion does not become creased under the forces from the user's thighs. On the other hand, the fold lines can provide controlled deformation of the article, that is to say the article is folded in a manner appropriate to the application. This means, for example, that the end portion having the ridge-like elevation does not collapse and become a valley under pressure from the sides, but instead it retains the ridge-like elevation against the user's body, which elevation fits in against the buttocks. If the fold lines are arranged on the underside of the article, a controlled deformation is obtained along the fold lines and the article is folded so that the parts of the underside of the article, to the side of a fold line, are pushed towards each other when the article is subjected to pressure from the user's thighs.

For this purpose, that is to say for obtaining controlled deformation, the fold lines can be produced, for example, by compression or removal of absorption material. The important point is to create a density in the area under the elastic which is different from the density in the surrounding areas. In this way, the area where the elastic is arranged will lift and form an elevation on the top side of the article. If the purpose of arranging fold lines is to give stability and firmness to the article, the fold lines must be arranged on the top side of the article. In this case, removal of material is not appropriate, but instead only compression, or other stiffening measures for creating the fold lines. Removing material would weaken the article and defeat the purpose.

The absorbent article can be secured in a conventional manner to the user's underwear with the aid of adhesive, for example. The adhesive can be arranged across the reverse side of the article, either along the margins or completely covering it. It is most advantageous, however, if the adhesive is arranged only in the end portions of the article. Such a construction allows the central portion to move freely and take up the menstruation fluid nearer its point of discharge from the body. A further alternative means of securing the article is to provide it with securing wings along each long side of the article. Examples of securing wings are found in EP 134,086. These securing wings are provided with adhesive surfaces which can be secured to the user's underwear. That is to say, the rest of the article is not provided with adhesive; In this way, an article is obtained with good securing properties and at the same time with good movement ability. Instead of adhesive, it is possible to use mechanical securing members such as friction fasteners or snap fasteners.

BRIEF DESCRIPTION OF THE FIGURES

The invention will be described in greater detail below with reference to the illustrative embodiments which are shown in the drawings.

FIG. 4a shows a section along the line IVa—IVa through the sanitary towel shown in FIG. 2.

FIG. 4b shows a section along the line IVb—IVb through the sanitary towel shown in FIG. 2.

FIG. 4c shows a section along the line IVc—IVc through the sanitary towel shown in FIG. 2.

FIG. 5 shows a folded-up sanitary towel according to the invention.

FIG. 6 shows a sanitary towel according to an alternative embodiment of the invention.

FIG. 7 shows a sanitary towel according to a second alternative embodiment of the invention.

FIG. 8 shows a sanitary towel according to a third alternative embodiment of the invention.

DETAILED DESCRIPTION OF THE FIGURES AND EMBODIMENTS

Figure 1:
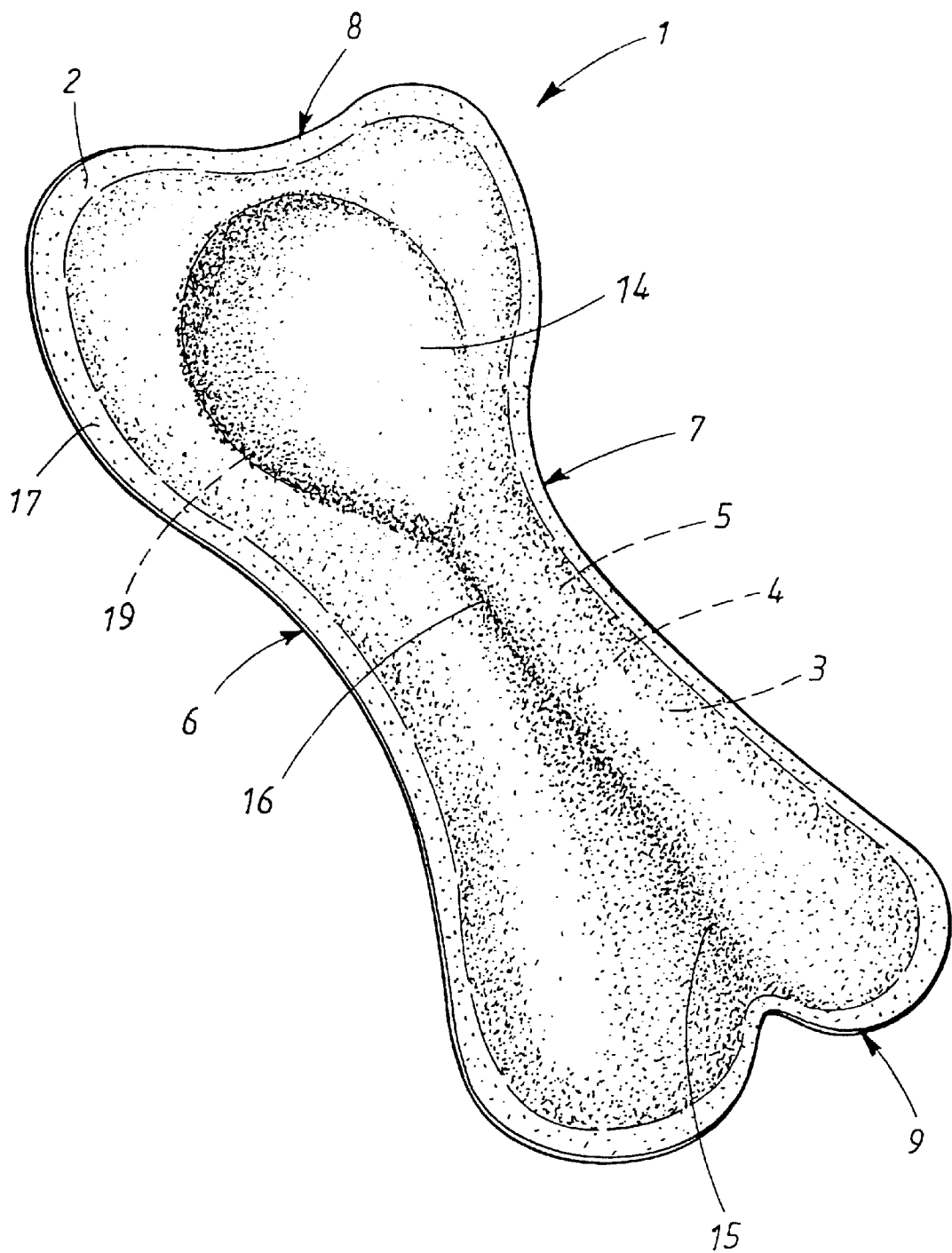
FIG. 1 shows a sanitary towel according to the invention seen in a perspective view.
Figure 2:
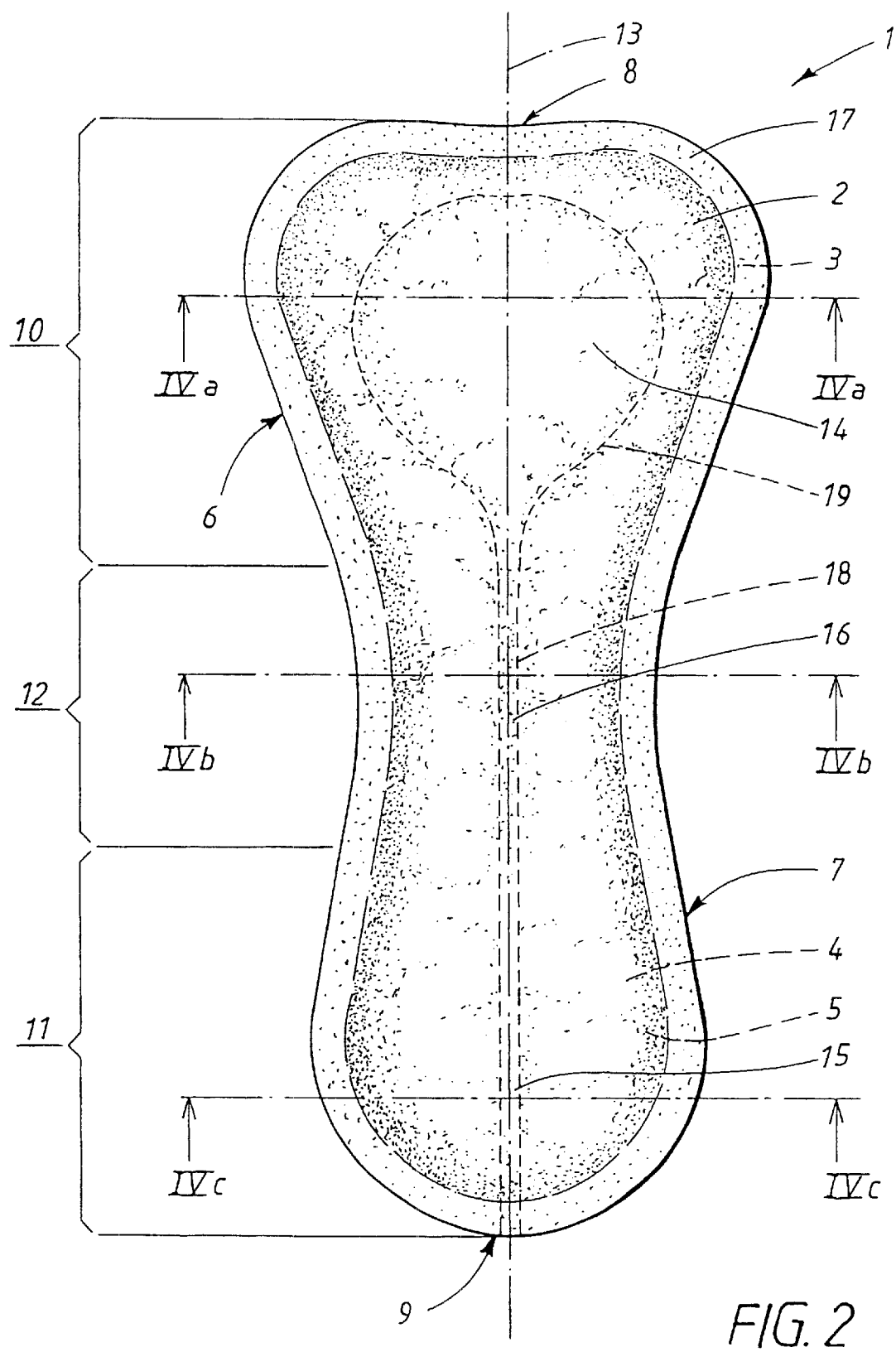
FIG. 2 shows a sanitary towel according to the invention seen from the side which during use is intended to be directed towards the user.

The sanitary towel 1 shown in FIGS. 1 to 4 comprises a liquid-permeable surface layer 2 arranged on that side of the sanitary towel 1 which during use is intended to be directed towards the user, a liquid-obstructing layer 3 arranged on that side of the sanitary towel 1 which during use is intended to be directed away from the user. Arranged nearest to the inside of the surface layer 2 is an intake layer 4, and between this and the liquid-obstructing layer 3 there is an absorption layer 5.

The material in the surface layer 2 can be, for example, a perforated plastic film, a net of plastic or textile material, a nonwoven or a laminate of, for example, a perforated plastic layer and a nonwoven layer. The plastic can be a thermoplastic, such as polyethylene. The nonwoven material can be of natural fibres, such as cellulose or cotton, or synthetic fibres, such as polyethylene, polypropylene, polyester, polyurethane, nylon or regenerated cellulose.

The main duties of the surface layer 2 of the sanitary towel are to lead the liquid in towards the intake layer 4, to be soft and comfortable against the user's body, and to prevent so-called rewetting, i.e. absorbed body fluid forcing its way back to the user's skin. For reasons of comfort, and in order to prevent skin irritation, it is important that the surface on that part of the sanitary towel bearing against the user's skin is kept as dry as possible during use. The user will also find a dry surface of the sanitary towel fresher and more comfortable during use, and a dry surface is more acceptable than a soiled, wet surface both from the purely visual point of view, and also when handling the sanitary towel when it needs to be changed.

The liquid-obstructing layer or reverse layer 3 consists of a liquid-impermeable material. Thin, liquid-impermeable plastic films are suitable for this purpose, but it is also possible to use materials which are liquid-permeable to start with but have been provided with a-coating of plastic, resin or other liquid-tight material. This prevents liquid from leaking out from the underside of the absorbent article. The barrier layer 3 can thus consist of any material which satisfies the criterion of liquid impermeability and has sufficient flexibility and skin compatibility for the purpose. Examples of materials suitable as barrier layers are plastic films. nonwovens and laminates thereof. The plastic film can; for example, be of polyethylene, polypropylene or polyester. The barrier layer can alternatively consist of a laminate of a liquid-impermeable plastic layer, directed towards the absorption body, and a nonwoven directed towards the user's underwear. Such a structure gives a leakproof barrier layer with a textile feel.

The role of the intake layer 4 of the sanitary towel is, in conjunction with the surface layer 2, to convey the liquid onwards to the absorption layer. Its role is two-fold: on the one hand, the liquid is to be led into the sanitary towel in such a way that leakage does not occur, and, on the other hand, the surface layer 2 must be kept dry for the user's comfort. It is expedient for the intake layer 4 to have a low density. An increasing density gradient is preferably formed down through the sanitary towel. That is to say, the surface layer 2 has a lower density than the intake layer 4, and the intake layer has a lower density than the absorption layer 5. Suitable materials for the intake layer 4 are, for example, wadding material and low-density airlaid pulp webs.

The absorption layer 5 is expediently made of cellulose pulp. The latter can be provided in the form of rolls, bales or sheets which, upon manufacture of the sanitary towel, are dry-defibred and converted in fluffed form to a pulp web, sometimes with admixture of so-called superabsorbents which are polymers with the ability to absorb several times their own weight of water or body fluid. An alternative to this is to dry-form a pulp web as has been described in WO 94/10956. If a dry-formed pulp web is used, it should be softened before being applied to a sanitary towel according to the invention. Alternatively, a strip of the fairly stiff material, measuring at most 45 mm in width, can be applied centrally on the sanitary towel. Other material of lesser stiffness is then applied over the whole width of the sanitary towel between the dry-formed strip and the surface layer 2. The softer absorption material, which can consist, for example, of the intake layer 4, forms the cup shape, while the underlying strip gives stability to the sanitary towel. Examples of other absorption materials that can be used are various types of natural fibres such as cotton fibres, peat moss or the like. It is of course also possible to use absorbent synthetic fibres or mixtures of natural fibres and synthetic fibres. The absorption material can also contain further components, such as shape-stabilizing members, liquid-spreading members, or binders such as, for example, thermoplastic fibres which have been heat-treated to hold short fibres and particles together in a coherent unit. It is also possible to use different types of absorbent foam material in the absorption layer.

The sanitary towel 1 has an essentially elongate shape with a longitudinal direction and a transverse direction and it has two long sides 6, 7 and two short sides 8, 9, two end portions 10, 11 and a central portion 12 situated between the end portions, and a centre line 13 extending in the longitudinal direction of the sanitary towel.

The central portion 12 and the end portions 10, 11 in each case represent about one third of the entire length of the sanitary towel 1. A normal sanitary towel is 18 to 30 cm long. This means that the respective lengths of the central portion 12 and the end portions 10, 11 is 6–10 cm. These values relate to a product which has been stretched out flat. Deviations from this model are of course possible. For example, the one end portion 10 can represent $4/10$ of the length of the sanitary towel, and the central portion 12 and the second end portion 13 can each represent $3/10$ of the length of the sanitary towel. In the case where the length of the sanitary towel 1 is 20 cm, this means that the one end portion 10 is 8 cm and the second end portion 11 and the central portion each have a length of 6 cm.

FIG. 1 shows a sanitary towel according to the invention seen in a perspective view. The sanitary towel 1 has a cup-shaped part 14 in the end portion 10 which during use is intended to be directed forwards on the user. Forwards on the user is intended to signify that the short side 8 of the end portion 10 will be that part of the sanitary towel which faces towards the user's abdomen. The opposite end portion 11, that is to say the end portion which is intended to be directed rearwards on the user, has a ridge-like elevation 15. Rearwards on the user is intended to signify that the short side 9 of the end portion 11 will be that part of the sanitary towel which lies towards the user's back. The cup-shaped part 14 and the ridge-like elevation 15 are to be arranged on that side of the article which has the surface layer 2 and which during use is intended to be directed towards the user's body.

The central portion 12 also has a ridge-like elevation 16, which represents a contiguous extension of the ridge-like elevation 15 of the end portion 11. The presence of a ridge-like elevation in the central portion 12 is advantageous since the vestibule of the user will be the part of the body which lies against the central portion 12. An elevation in this portion can be particularly important for preventing leakage, since the sanitary towel at an early stage is able to take up the menstruation fluid as it leaves the body.

Figure 3:
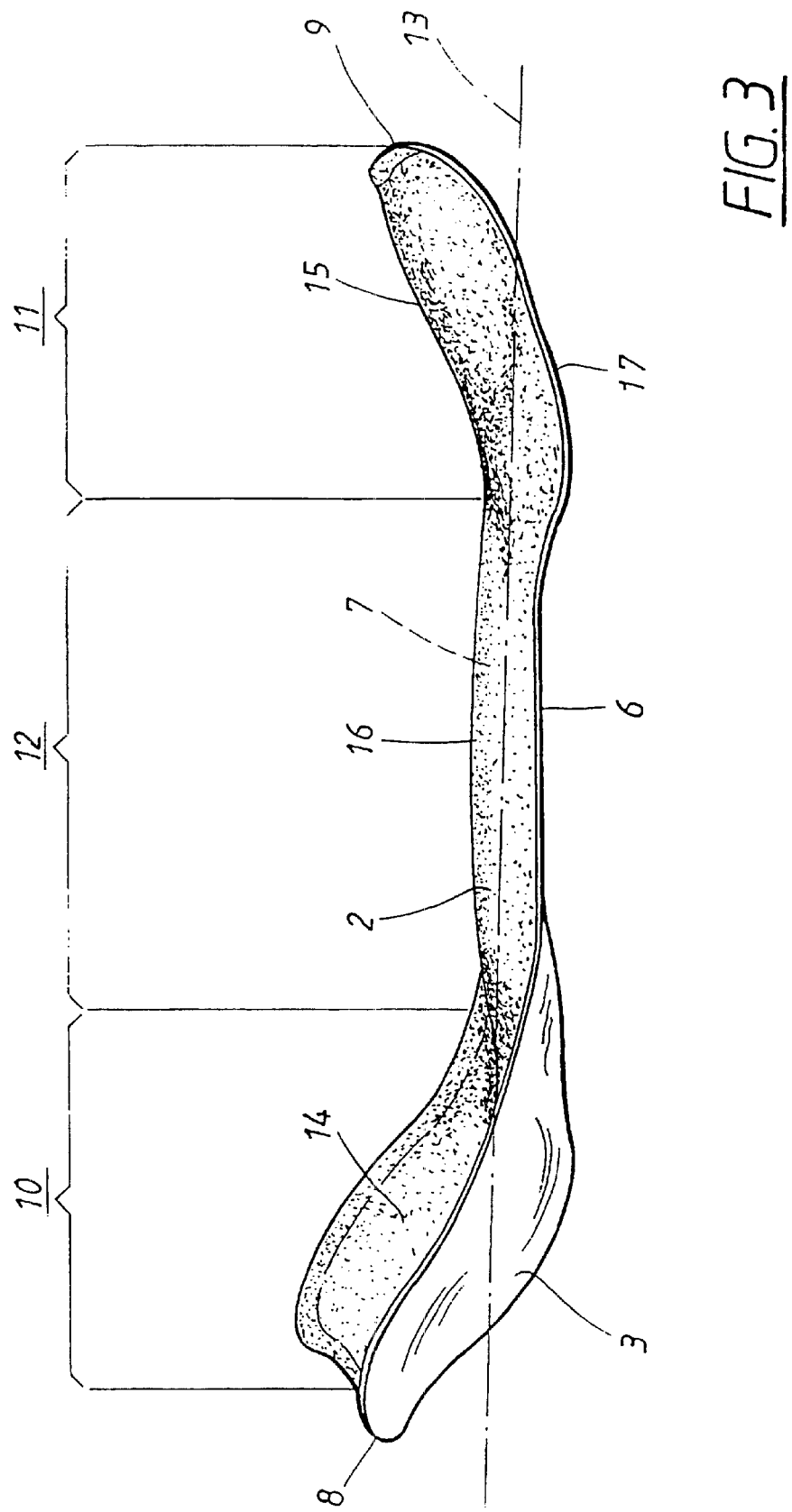
FIG. 3 shows a sanitary towel according to the invention seen from one long side.

FIG. 3 shows a sanitary towel 1 seen from one long side 6. The cup-shaped front end portion 10, the ridge-like elevation 16 of the central portion 12 and the ridge-like elevation 15 of the rear end portion 11 are shown here. As can be seen in the Figure, the ridge-like elevation 15 of the end portion 11 has a steeper inclination in relation to the centre line 13 of the sanitary towel than does the ridge-like elevation 16 of the central portion 12. This is of course adapted to the curvatures of the corresponding female anatomy. While the contour of the elevation 16 of the central portion can be essentially parallel with the centre line 13 or slope slightly in relation to said centre line 13, it is important that the elevation 15 of the end portion 11 slopes more steeply in relation to the centre line 13, seen from one long side 6 of the sanitary towel, so that said sanitary towel 1 will fit the cleft between the user's buttocks. For the central portion 12 of the sanitary towel to fit the vestibule, the curvature in the transverse direction of the article is the most important, that is to say the cross-section has a ridge-like elevation.

FIGS. 4a to 4c show a cross-section through the sanitary towel, seen from the front short side 8. The two outer layers 2, 3 are connected to each other outside the intake layer 4 and the absorption layer 5 in a seam 17 located along the periphery of the sanitary towel. For the sake of simplicity, only the actual cross-sectional surface is shown and not rearwardly projecting parts. FIG. 4a shows a cross-section through the end portion 10 of the sanitary towel 1 which has the cup-shaped appearance or portion 14. FIG. 4b shows a cross-section through the central portion 12. The ridge-like elevation 16 of the central portion and the likewise ridge like cross-section of the central portion can be seen here. FIG. 4c shows a cross-section of the end portion 11, which has the ridge-like elevation 15.

Arranged between the intake layer 4 and the absorption layer 5 of the sanitary towel 1 there is an elastic thread 18. In order to obtain the above-described three-dimensional anatomical configuration around the user's mons pubis, the elastic thread 18 is arranged in a loop 19 in the end portion 10 which during use is intended to be directed forwards on the user. In order to obtain the anatomical fit in the end portion 11 which during use is intended to be directed rearwards on the user, that is to say the end portion which is to fit in the cleft between the user's buttocks, the elastic thread 18 is arranged in an essentially straight line along the centre line 13 of the article. The elastic thread 18 consists of a single continuous thread. This means that the elastic thread lies double along the central portion 12 and the end portion 11 which has the ridge-like elevation 15. This is a simple way of arranging the elastic. A further advantage is that it is easy to produce a pronounced elevation in the end portion 11 which has the ridge-like elevation 15. It is of course possible to arrange the elastic in another way. For example, two separate elastic threads can be used, where one thread forms the loop in the cup-shaped end portion 10 of the sanitary towel and the other thread is laid straight across the central portion 12 and the end portion 11 along the centre line 13.

The elastic thread 18 can be made of conventional elastic material. The material of the elastic thread 18 need not be elastic per se, and instead the elastic property can be achieved by working a nonelastic material. The elastic does not have to be shaped as a thread and can be band-shaped, for example.

FIG. 5 shows a sanitary towel according to the invention which has been folded up so that it can be placed, for example, in a single pack. The sanitary towel 1 is folded in three, the front end portion 10 with the cup.44 shaped part 14 being first folded inwards across that side of the sanitary towel which has the surface layer 2. After this, the rear end portion 11 with the ridge-like elevation is folded inwards across the front end portion 10 so that the surface layer 2 on the rear end portion 11 is facing the reverse layer 3 of the front end portion 10. By folding the sanitary towel so that the reverse layer 3 faces outwards, the stress on the elastic is relaxed and the useful life of the product is extended.

FIG. 3 shows the sanitary towel 1 with the elastic thread 18 arranged between the intake layer 4 and the absorption layer 5. This is only one example of where the elastic thread 18 can be arranged in the sanitary towel 1. It is possible to place the elastic thread 18 anywhere between the surface layer 2 and the reverse layer 3. Of course, this also applies if the elastic were to be arranged in a form other than a thread. The elastic is secured to the sanitary towel with the aid of adhesive, for example, or by ultrasonic welding. The elastic is secured to the sanitary towel in the prestressed state or is alternatively activated so that it can be tensioned, for example by heating, after application.

FIGS. 6 to 8 show alternative embodiments of the invention in which the elastic does not constitute a continuous loop.

FIG. 6 shows an embodiment of the invention according to which the elastic 18 is arranged in a U-shaped loop 20 in the end portion 10 which has the cup-shaped part 14. That is to say, the elastic 18 broadly speaking follows the outer contour of the end portion 10 and the opening of the U-shape faces towards the central portion 12 of the sanitary towel 1. On the central portion 12 of the sanitary towel, and on the end portion 11 having the ridge-like elevation 15, the elastic is arranged as a straight thread 21, that is to say as a straight line, along a longitudinal centre line 13 of the sanitary towel.

FIG. 7 shows another embodiment of the invention according to which the elastic 18 is arranged in two mirror-image loops 22, 23 which each follow the outer contour of the long sides of the end portion 10 which has the cup-shaped part 14. On the central portion 12 of the sanitary towel, and on the end portion 11 which has the ridge-like elevation 15, the elastic 18 is arranged, along a longitudinal centre line 13 of the sanitary towel, in two parallel straight threads 22a, 23a which are in each case contiguous with the respective loop 22, 23 in the other end portion 10 of the sanitary towel. The two elastic loops 22, 23 are arranged symmetrically around the longitudinal centre line 13 through the whole sanitary towel.

FIG. 8 shows an embodiment of the invention according to which the elastic 18 is arranged in two mirror-image, crescent-shaped loops 24, 25 in the end portion 10 of the sanitary towel having the cup-shaped part 14. On the central portion 12 and the end portion 11 having the ridge-like elevation 15, the elastic is arranged in a straight thread 26 running along the longitudinal centre line of the sanitary towel.

Figure 9:
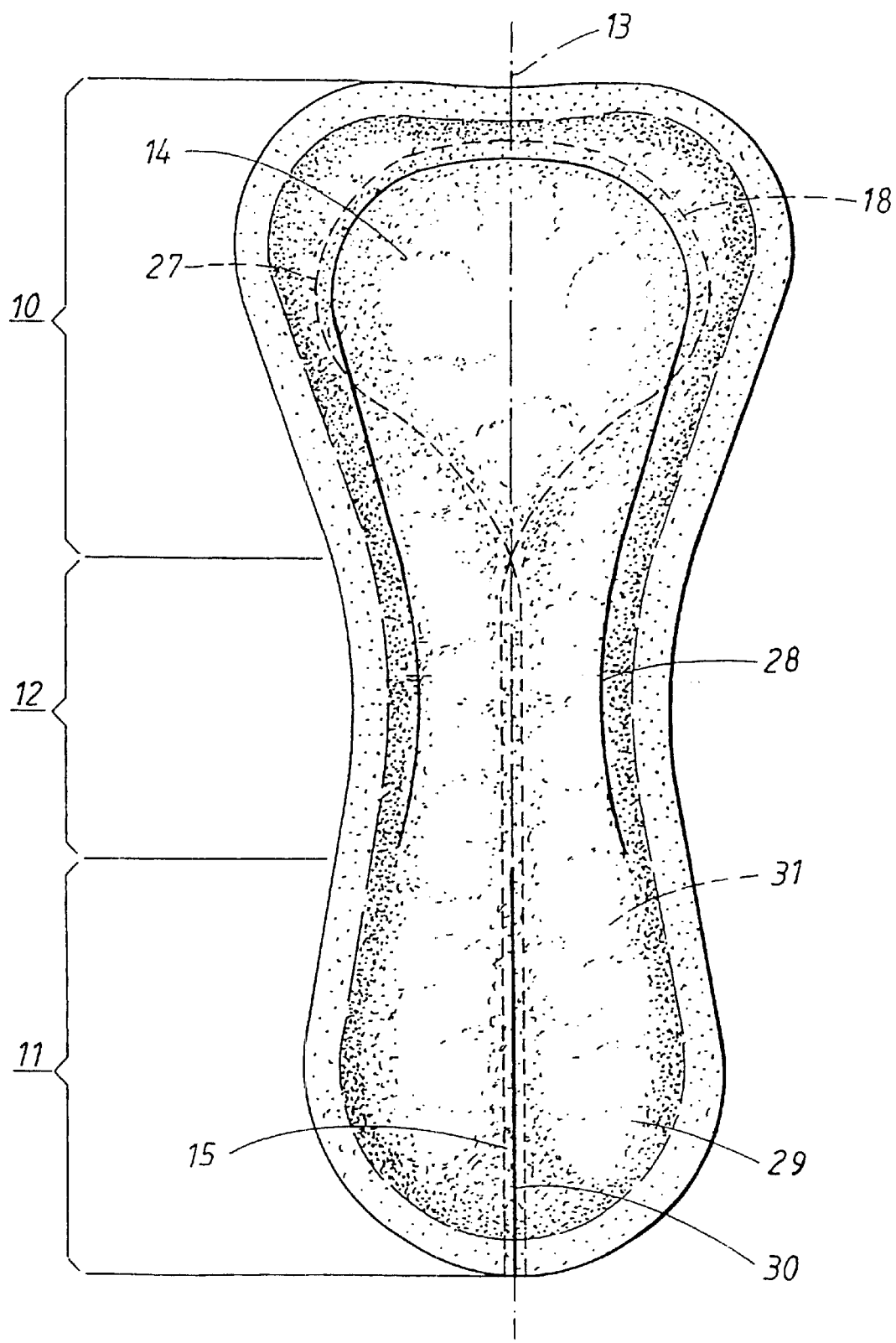
FIG. 9 shows a sanitary towel according to a fourth alternative embodiment of the invention.
Figure 10:
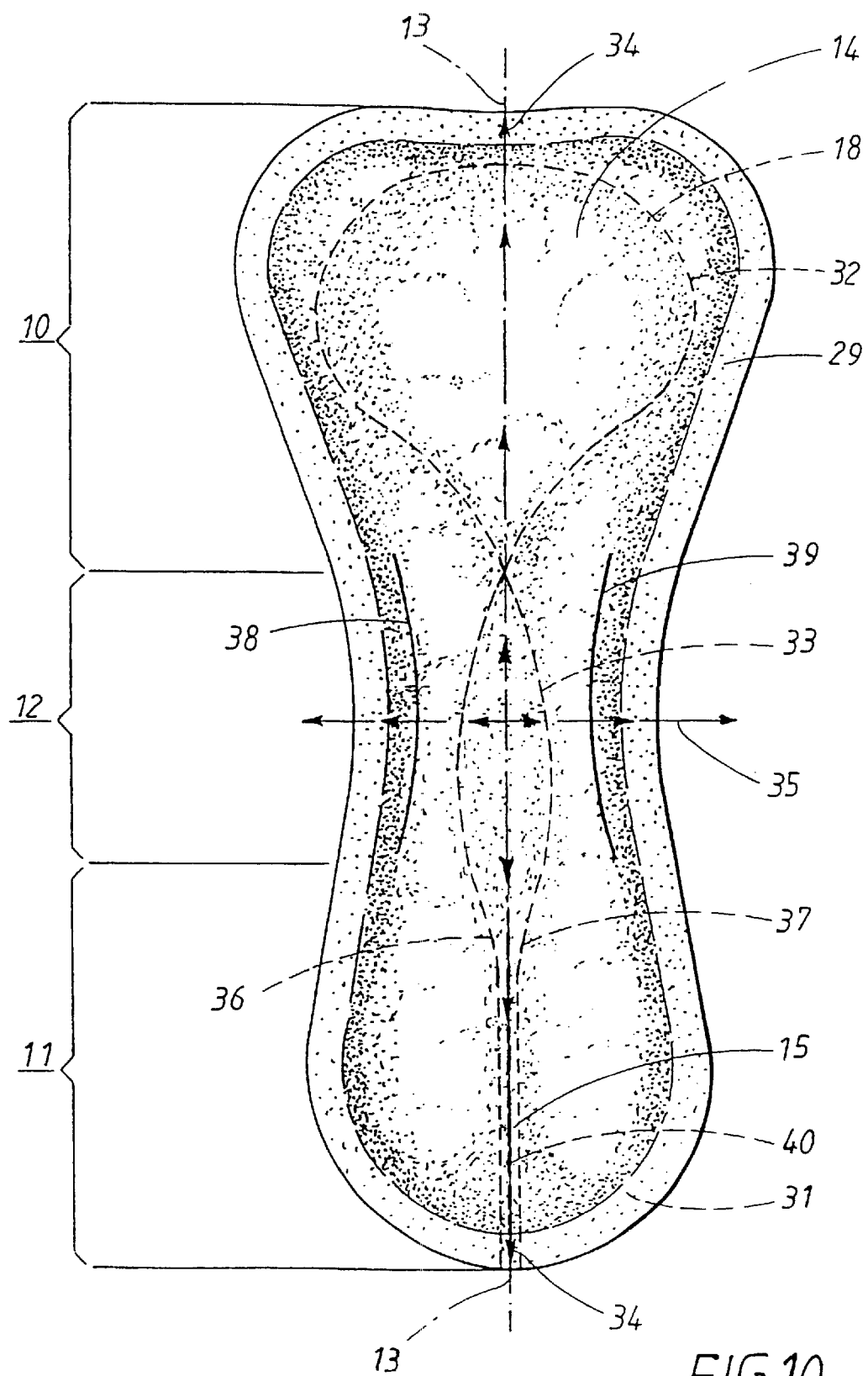
FIG. 10 shows a sanitary towel according to a fifth alternative embodiment of the invention.
Figure 11:
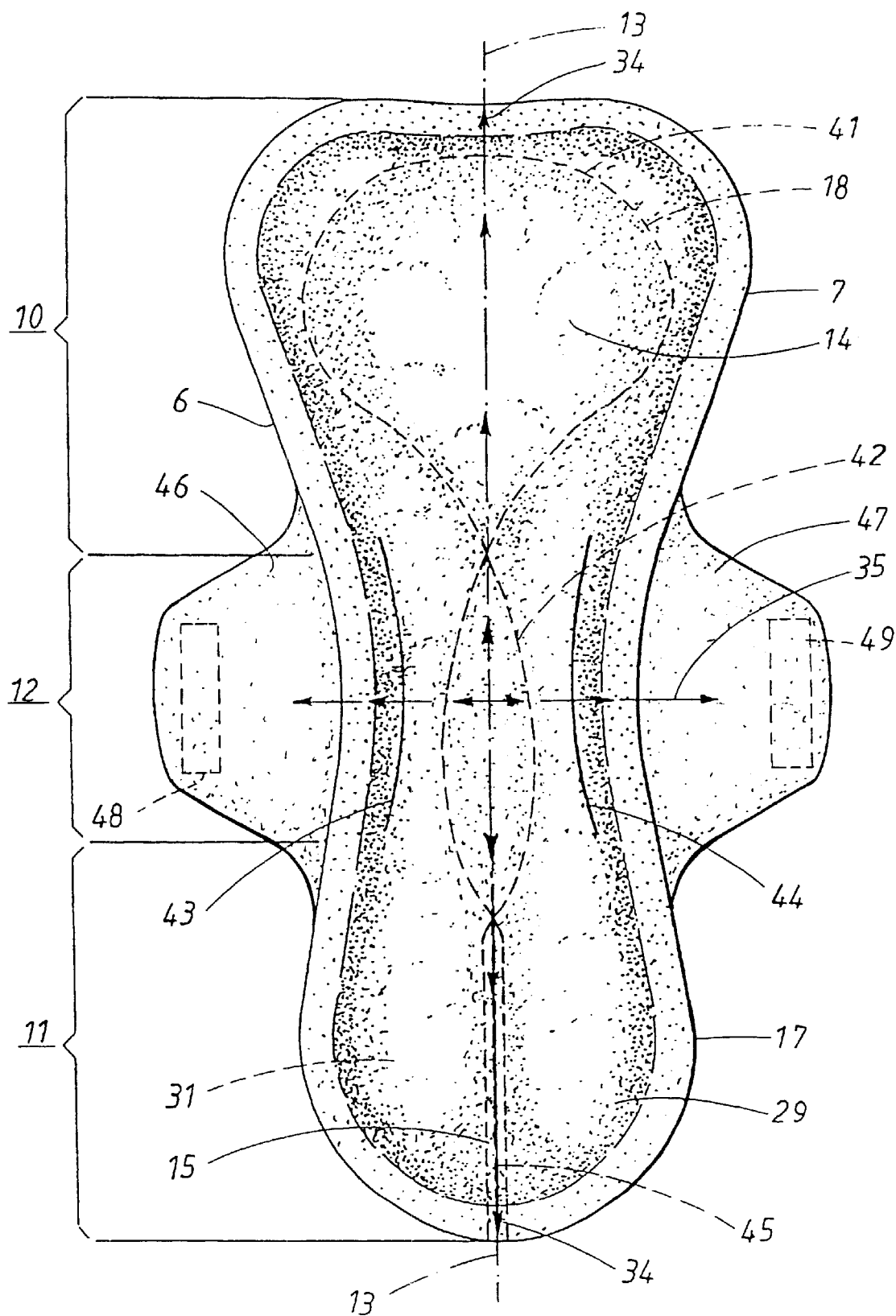
FIG. 11 shows a sanitary towel according to a sixth alternative embodiment of the invention.

FIGS. 9 to 11 show embodiments of the invention in which the elastic is arranged as a single continuous loop. The sanitary towel according to FIGS. 9 to 11 is hourglass-shaped with a narrower central portion and wider end portions.

FIG. 9 shows a sanitary towel according to the invention on which the elastic 18 is arranged in an essentially circular loop 27 in the end portion 10 which has the cup-shaped part 14. At the transition between the end portion 10 which has the cup-shaped part 14 and the central portion 12, the elastic thread 18 crosses over and then runs parallel along a longitudinal centre line 13 of the sanitary towel. According to this embodiment, the central portion 12 has no ridge-like elevation as the elastic thread 18 has not been prestressed across the central portion 12. The sanitary towel in FIG. 9 has a fold line 28 arranged in the end portion 10 which has the cup-shaped part 14. The fold line 28 follows the outer contour of the sanitary towel in the end portion 10 which has the cup-shaped part 14 and in the central portion 12. In these portions the fold line 28 is made on the top side 29 of the sanitary towel. This ensures a controlled deformation of the end portion 10 into a cup shape.

In the central portion 12 where the elastic 18 is not tensioned, the fold line 28 gives increased stability and functions as a barrier against leakage. On the end portion 11 which has the ridge-like elevation 15, a fold line 30 is arranged along the elastic 18. Here, however, the fold line is arranged on the underside 31 of the sanitary towel in order to ensure a controlled deformation of the end portion 11 so that the elevation 15 against the user's body is obtained.

FIG. 10 shows a sanitary towel according to the invention on which the elastic 18 is arranged in an essentially circular loop 32 in the end portion 10 which has the cup-shaped part 14. At the transition between the end portion 10 which has, the cup-shaped part 14 and the central portion, the elastic thread 18 crosses over to form another loop 33 across the central portion 12. The loop 33 across the central portion 12 has approximately the same extent or length in the longitudinal direction 34 of the sanitary towel as does the loop 32 in the end portion 10, but a smaller extent in the transverse direction 35 of the sanitary towel. The loop 33 in the central portion 12 has an oval shape. At the transition to the end portion 11 which has the ridge-like elevation 15, the distance between the parts of the elastic thread 18 decreases so as to run in parallel threads 36, 37 across the said end portion 11 along a longitudinal centre line 13 of the sanitary towel. The sanitary towel in FIG. 10 has fold lines 38, 39 in its central portion. The fold lines 38, 39 follow, or have the same contour as, the outer contour of the sanitary towel and are arranged approximately equidistant between the long sides of the sanitary towel and the elastic loop 33. The fold lines 38, 39 are arranged on the top side 29 of the sanitary towel in its central portion 12 and give the latter increased stability and at the same time they function as barriers against leakage. In the end portion I11 which has the ridge-like elevation 15, a fold line 40 is arranged on the underside 31 of the sanitary towel and along the longitudinal centre line of the sanitary towel. The fold line 40 contributes to ensuring that the ridge-like elevation 15 is formed.

FIG. 11 shows a sanitary towel according to the invention on which the elastic 18 is arranged in an essentially circular loop 41 in the end portion 10 which has the cup-shaped part 14. At the transition between the end portion 10 which has the cup-shaped part 14 and the central portion 12, the elastic thread 18 crosses over to form another loop 42 across the central portion. The loop 42 across the central portion 12 has approximately the same extent or length in the longitudinal direction 34 of the sanitary towel as does the loop 41 in the end portion 10, but it has a smaller extent in the transverse direction 35 of the sanitary towel than does the loop 41 in the end portion 10. The loop 42 in the central portion 12 has an oval shape. The sanitary towel in FIG. 11 has fold lines 43, 44 in its central portion. The fold lines 43, 44 follow, or have the same contour as, the outer contour or seam 17 of the sanitary towel and are arranged approximately equidistant between the long sides of the sanitary towel and the elastic loop 42. The fold lines 43, 44 are arranged on the top side 29 of the sanitary towel in its central portion 12 and give the latter increased stability and at the same time they unction as barriers against leakage. In the end portion 11 which has the ridge-like elevation 15, a fold line 45 is arranged on the underside 31 of the sanitary towel and along the longitudinal centre line 13 of the sanitary towel. The fold line 45 contributes to ensuring that the ridge-like elevation 15 is formed. The sanitary towel according to FIG. 11 has two securing wings 46, 47 arranged along the long sides 6, 7 of the sanitary towel in the central portion 12 of the sanitary towel. The securing wings 46, 47 are each provided with adhesive areas 48, 49 arranged on the underside 31 of the sanitary towel. These adhesive areas are intended to be secured on the user's underwear. The other parts of the underside 31 of the sanitary towel are free of adhesive. Since the sanitary towel is secured to the user's underwear only at the securing wings 46, 47, the central portion 12 of the sanitary towel with the ridge-like elevation 16 has good mobility in order to adapt to the body. This also makes it easier for the cup-shaped part 14 on the end portion 10 to surround the mons pubis and makes it easier for the ridge-like elevation 15 on the end portion 11 to fit in against the user's buttocks under the effect of the shear which occurs when the user is walking or cycling.

In all the illustrated embodiments of the invention, the sanitary towel can have securing wings with adhesive on these alone. Alternatively, according to all the embodiments, the entire underside of the sanitary towel can be provided with adhesive, or the adhesive is applied in the areas only under the end portions.

In the illustrative embodiments, the fold lines are shown on sanitary towels with a continuous loop of elastic. Of course, the fold lines function equally well on embodiments with divided elastic.

For the sake of simplicity, the elastic is indicated as an elastic thread in the illustrative embodiments. However, it is equally possible to choose elastic in another form, for example in the form of a band, for all the embodiments.

All the illustrated sanitary towels according to the invention can have a ridge-like elevation on the central portion if so desired, since there is elastic in the central portion of the sanitary towels in all the examples shown. The elevation will look different since the arrangement of the elastic is different. Perfect adjustment to the body is weighed against production factors and, as has already been mentioned, user comfort. It is also possible to have elastic only in the two end portions if no elevation is wanted in the central portion.

For the sake of simplicity, the sanitary towel shown in the figures is of conventional structure with a liquid-permeable surface material, a liquid-obstructing reverse layer, an intake layer and an absorption layer. However, this is not essential to the invention. It is possible to omit the intake layer and have only a surface material, absorption layer and reverse. It is also possible to omit the liquid-obstructing layer, for example when producing a panty liner where the amounts of fluid excreted are not so great. In certain applications it is also possible to exclude a surface layer of conventional type. In this case the intake layer is arranged in such a way that the necessary surface dryness is still achieved. Different combinations of the described illustrative embodiments are also possible within the scope of the invention.

What is claimed is:

1. An absorbent article, such as a sanitary towel, an incontinence protector or a pantyliner, which article has an essentially elongate shape, with a longitudinal direction (34) and a transverse direction (35), a top side which is intended during use to be directed towards a user, and an underside which is intended during use to be directed away from the user, and having two end portions (10, 11) and a central portion (12) situated between the end portions (10, 11), said article further having a cup-shaped part at the one end portion (10) and a ridge-like elevation (15) at the other end portion (11), characterized in that the article is provided with elastic (18), said elastic being arranged in an essentially straight line along the centre line (13) of the article in the end portion (11) which has the ridge-like elevation (15) and comprising elastic (19; 20; 24,25; 27) being arranged in a crescent-shaped loop on either side of the longitudinal centre line of the article in the end portion (10) which has the cup-shaped part (14).

2. An absorbent article according to claim 1, characterized in that the elastic (18) is arranged in a loop (19) in the end portion (10) which has a cup-shaped part (14).

3. An absorbent article according to claim 1 or 2, characterized in that the central portion (12) has a ridge-like elevation (16).

4. An absorbent article according to claim 3, characterized in that the elastic (18) in the central portion (12) is arranged in an essentially straight line along the centre line (13) of the article.

5. An absorbent article according to claim 3 or 4 and having two long sides (6, 7) extending in the longitudinal direction, and two short sides (8, 9) extending in the transverse direction, characterized in that the ridge-like elevation (15) in the end portion (11) has a steeper inclination towards the centre line (13) of the article than does the ridge-like elevation (16) in the central portion (12), as seen from the long side (6) of the article.

6. An absorbent article according to any one of the preceding claims, characterized in that the elastic (18) is arranged as a continuous thread or band running in a loop through the article.

7. An absorbent article according to claim 6, characterized in that the elastic (18) is laid overlapping at the transition between the end portion (10) which has the cup-shaped part (14) and the central portion (12).

8. An absorbent article according to claim 6 or 7, characterized in that the elastic (18) is laid overlapping at the transition between the central portion (12) and the end portion (11) which has the ridge-like elevation (15).

9. An absorbent article according to any one of the preceding claims, characterized in that the article has at least one fold line (30).

10. An absorbent article according to claim 9, characterized in that a fold line (30) is arranged on the underside of the article below the ridge-like elevation (15) in the end portion (11).

11. An absorbent article according to claim 9 or 10, characterized in that a fold line (28) is arranged on the top side of the article, essentially following the contour of the elastic (18) of the cup-shaping elastic (19; 20; 24, 25; 27) in the end portion (10) which has the cup-shaped part (14).

* * * * *